US00PP23507P2

(12) United States Plant Patent
Kardos et al.

(10) Patent No.: US PP23,507 P2
(45) Date of Patent: Apr. 2, 2013

(54) ***GARDENIA JASMINOIDES* PLANT NAMED 'DOUBLE MINT'**

(50) Latin Name: *Gardenia jasminoides*
Varietal Denomination: Double Mint

(75) Inventors: Joshua H. Kardos, Watkinsville, GA (US); Michael A. Dirr, Bogart, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/374,635

(22) Filed: Jan. 4, 2012

(51) Int. Cl.
*A01H 5/00* (2006.01)

(52) U.S. Cl. ..... Plt./255

(58) Field of Classification Search ..... Plt./255
See application file for complete search history.

(56) References Cited

PUBLICATIONS

Lantana Catalog Page (distributed at a trade show Jan. 5, 2011) "*Gardenia* Double Mint", 1 pg.
Plant Introductions, Inc. webpage, (downloaded Dec. 30, 2011) "*Gardenia jasminoides* selections", http://www.plantintroductions.com/gardeniaselections.html, 3 pgs.

*Primary Examiner* — Annette Para
(74) *Attorney, Agent, or Firm* — Lathrop & Gage LLP

(57) ABSTRACT

A new and distinct cultivar of *Gardenia jasminoides* plant named 'Double Mint', characterized by fragrant, double white flowers, abundant flowers in spring with reblooming to fall, lustrous, dark green foliage, compact rounded growth habit, cold hardy to USDA Hardiness Zone 7, and resistance to root rot diseases.

3 Drawing Sheets

Genus and species of plant claimed: *Gardenia jasminoides*.

Variety denomination: 'Double Mint'.

BACKGROUND OF THE INVENTION

The present invention relates to a new and distinct cultivar of *Gardenia jasminoides*, a member of the Rubiaceae family, hereinafter referred to by its cultivar name 'Double Mint'. This cultivar is grown primarily as an ornamental for landscape use and for use as a potted plant.

The new *Gardenia* cultivar originated from an open-pollination of *Gardenia jasminoides* 'Chuck Hayes' (U.S. Plant Pat. No. 8,755) as part of a planned breeding program to develop reblooming, double-flowered *Gardenias*. The cultivar 'Double Mint' originated and was discovered in a cultivated environment in an outdoor nursery in Watkinsville, Ga.

'Double Mint' has been asexually reproduced by softwood cuttings in Watkinsville, Ga. since 2008, and the characteristics of the cultivar have been stable and reproduced true-to-type in successive vegetative generations.

SUMMARY OF THE INVENTION

'Double Mint' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'Double Mint' from all other varieties in commerce known to the inventor. 1) Fragrant, double white flowers. 2) Abundant flowers in spring with reblooming to fall. 3) Lustrous, dark green foliage. 4) Compact rounded growth habit. 5) Cold hardy to USDA Hardiness Zone 7. 6)

Resistance to root rot diseases. There are no other cultivars of *Gardenia jasminoides* with this combination of characteristics known to the inventor.

'Double Mint' is distinguished from its female parent, 'Chuck Hayes', by its growth habit, foliage size, and winter foliage color. 'Double Mint' has a smaller, more compact growth habit than 'Chuck Hayes'. 'Double Mint' has smaller foliage than 'Chuck Hayes'. 'Double Mint' has foliage that maintains its dark green color during winter, whereas 'Chuck Hayes' has foliage that often turns yellow-green in winter.

'Double Mint' can be compared to 'Crown Jewel' (U.S. Plant Pat. No. 19,896), but differs in the following characteristics. 'Double Mint' has a rounded growth habit, whereas 'Crown Jewel' has a spreading growth habit. 'Double Mint' has smaller foliage than 'Crown Jewel'. 'Double Mint' reblooms from spring to fall, whereas 'Crown Jewel' only flowers in spring. 'Double Mint' is more resistant to root rot in production than 'Crown Jewel'.

'Double Mint' can be compared to 'Leeone' (U.S. Plant Pat. No. 21,983), but differs in the following characteristics. 'Double Mint' has a rounded growth habit, whereas 'Leeone' has an upright, globose growth habit. 'Double Mint' has smaller foliage than 'Leeone'. 'Double Mint' has smaller flowers than 'Leeone'. 'Double Mint' flowers more abundantly than 'Leeone'.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Gardenia*.

DETAILED DESCRIPTION

Figure 1:
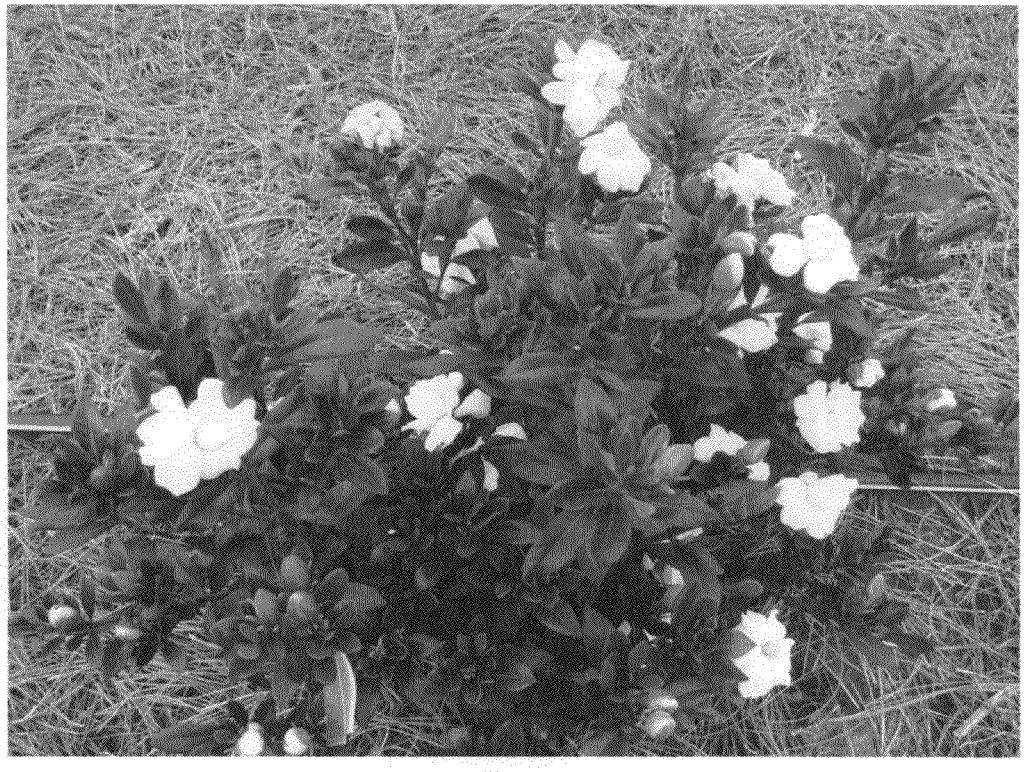
FIG. 1 shows the overall appearance of a plant of 'Double Mint' planted in the ground.
Figure 2:
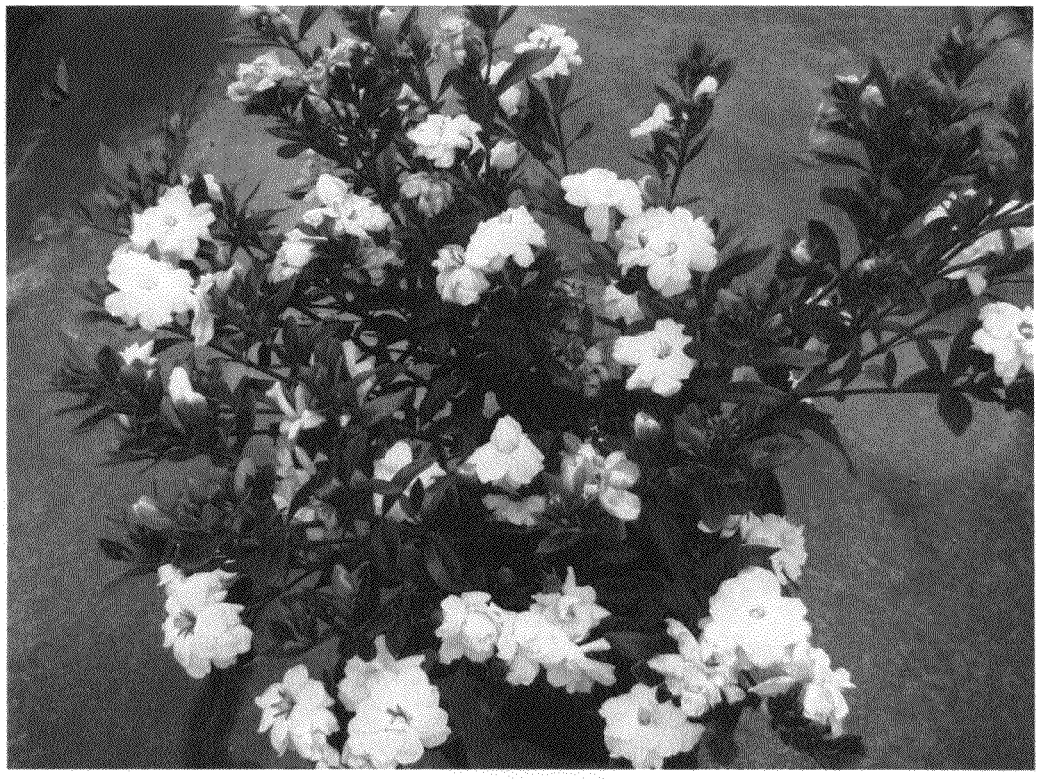
FIG. 2 shows the overall appearance of a plant of 'Double Mint' in a container.
Figure 3:
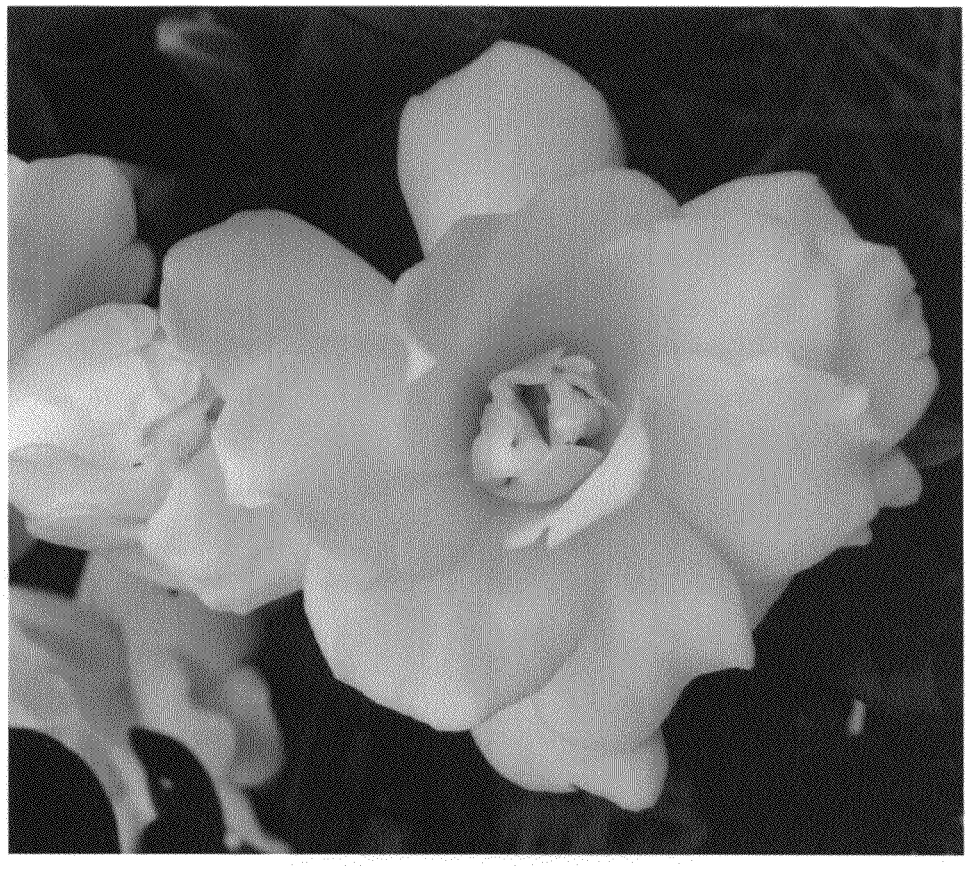
FIG. 3 shows a close-up view of a flower of 'Double Mint'.

In the following description, color references are made to The Royal Horticultural Society Colour Chart, 2001 Edition, except where general terms of ordinary dictionary significance are used. Plants used for the description were approximately 2 years old and were grown in 8 L containers in full sun under outdoor conditions in Watkinsville, Ga.

Botanical classification: 'Double Mint' is a cultivar of *Gardenia jasminoides*.

Parentage: The current variety is a progeny from an open-pollination of *Gardenia jasminoides* 'Chuck Hayes' (U.S. Plant Pat. No. 8,755).

Plant description: The claimed variety is a freely branching, rounded, evergreen shrub. The plant is hardy in USDA Zones 7 to 9.

*Propagation*.—Stem cuttings. Time to initiate roots in summer: about 4 weeks.

*Root description*.—Numerous, fibrous, and well-branched.

*Plant size*.—About 68 cm high from the soil level to the top of the foliage and about 70 cm wide after about 4 years.

*First year stems*.—Having a diameter of about 3 mm. Shape: round. Pubescence: finely hairy.

*First year stem color* (*young*).—146B. Color (woody): 199A.

*Stem strength*.—Flexible when young, more easily broken once mature.

*Internode length*.—About 2.3 cm.

*Second year and older stems*.—Have a diameter of about 5 mm or more. Shape: round. Pubescence: none.

*Second year and older stem color*.—N199B.

*Bark*.—Some stringy exfoliation beginning on second year stems.

*Trunk diameter*.—About 1.7 cm at the soil line. Color: N200A.

Vegetative bud description:

*Vegetative buds*.—Arrangement: opposite. Shape: conical, single-scaled. Size: about 3 mm in length, about 1 mm in width; Color: 143A.

Foliage description:

*Arrangement*.—Opposite. Length: about 4.2 cm. Width: about 1.7 cm.

*Shape*.—Elliptical. Apex: acuminate. Base: cuneate. Margin: entire to revolute.

*Texture* (*upper and lower surfaces*).—Glabrous, lustrous, no pubescence.

*Venation*.—Pinnate. Venation color (upper and lower surfaces): 144B.

*Color of emerging foliage*.—144A on the upper surface, and 144B on the lower surface. Color of mature foliage: 147A on the upper surface, and 146B on the lower surface.

*Petiole length*.—About 1 mm. Petiole diameter: about 2 mm. Petiole texture: glabrous. Petiole color (upper and lower surfaces): 144B.

Flower description:

*Flower type and habit*.—Flowers are borne singly at the terminals and the crotches where two stems divide. Individual flowers are showy for about 2 days and remain on the plant for about 1 to 2 weeks after they have senesced. Bloom period: spring to frost. Flowers are produced abundantly from May to June, and then sporadically through November in Watkinsville, Ga. Fragrance: Exceedingly sweet fragrance.

*Flower diameter*.—About 5 cm. Height or depth: about 4 cm.

*Flower bud diameter*.—About 1 cm. Flower bud length: about 2.5 cm. Flower bud shape: oblong. Flower bud color: 144A.

*Calyx*.—About 2.5 cm in length, about 1.5 cm in width, and 144A in color.

*Pedicels*.—About 2 cm in length, glabrous, and 144A in color.

Petals:

*Quantity*.—6 to 8 true petals and 16 to 18 peataloids per flower.

*True petal length*.—About 2.4 cm. Width: about 2.3 cm. Shape: obovate with entire, undulating margins and overlapping in arrangement to form a whorl. Texture: thick, glabrous. Color: at peak bloom the upper and lower surfaces are 155C aging to 11C and eventually to N199D before dehiscing.

*Petaloid petal length*.—Ranges from 1.5 to 2.5 cm, becoming smaller toward the center of the flower. Width: ranges from 1.1 to 2.1 cm, becoming smaller toward the center of the flower. Shape: Texture: thick, glabrous. Color: at peak bloom the upper and lower surfaces are 155C aging to 11C and eventually to N199D before dehiscing.

Stamens:

*Quantity*.—4 to 6 per flower, sometimes petaloid or malformed. There is no separate filament structure present, instead the anthers are fused to the base of the petals. Anthers: about 8 mm long and about 2 mm wide. Color: 199A. Pollen: is either nonexistent or produced in small quantities and color is 8B.

Pistils:

*Quantity/arrangement*.—One per flower, inferior. Pistil length: about 1.8 cm. Pistil diameter: about 4 mm. Stigma shape: obovate, about 7 mm length and about 4 mm in diameter. Stigma color: 1C. Style: color is 154D, about 6 mm in length, and about 1.5 mm in width. Ovary: color is 2C, about 5 mm in length, about 4 mm in width, elliptoid in shape, and contains many (50 or more) very small (less than 1 mm) ovules.

Fruit:

*Type/appearance*.—Six-winged berry, oval in shape. Fruit length: about 2.5 cm. Fruit diameter: about 2 cm. Fruit color at maturity: N170A. Quantity: fruit is rarely produced and the number of fruit per plant varies depending on the size and maturity of the plant. Seeds: rounded in shape, about 2.5 mm in diameter, 164C in color, and each berry contains many seeds, about 100 or more.

Disease/pest resistance: No specific pest or disease resistance or susceptibility has been observed.

I claim:

1. A new and distinct *Gardenia augusta* plant named 'Double Mint', substantially as illustrated and described herein.

* * * * *